United States Patent [19]
Alpern

[11] Patent Number: 5,131,533
[45] Date of Patent: Jul. 21, 1992

[54] NEEDLE PARK

[75] Inventor: Marvin Alpern, Geln Ridge, N.J.

[73] Assignee: Ethicon, Inc., Somerville, N.J.

[21] Appl. No.: 751,039

[22] Filed: Aug. 28, 1991

[51] Int. Cl.$^5$ ............................................. A61B 17/06
[52] U.S. Cl. ................................... 206/63.3; 206/380
[58] Field of Search ................. 206/63.3, 380, 382, 206/381, 339

[56] References Cited

U.S. PATENT DOCUMENTS

| | | | |
|---|---|---|---|
| 4,424,898 | 1/1984 | Thyen et al. | 206/63.3 |
| 4,961,498 | 10/1990 | Kalinski et al. | 206/339 |
| 4,967,902 | 11/1990 | Sobel et al. | 206/63.3 |
| 5,052,551 | 10/1991 | Cerwin et al. | 206/63.3 |
| 5,056,658 | 10/1991 | Sobel et al. | 206/63.3 |

*Primary Examiner*—William I. Price
*Attorney, Agent, or Firm*—James Riesenfeld

[57] ABSTRACT

A needle park for a package that holds one or more surgical needles and sutures has a generally planar base and two collinear walls that are perpendicular to the base. A cutout near one end of the first wall separates an end section of the wall from the base and separates all but a top segment of the end section from the rest of the wall. The second wall is separated from the end section by a gap. The end section and top segment of the first wall form a hinge that permits a needle to be held in the gap between the walls. In an alternative embodiment, both walls have cutouts and resultant hinges, thus permitting the needle park to hold needles of larger diameter. Preferably, the material of the needle park is a moldable thermoplastic. The needle park is inexpensive to fabricate and permits a needle in a broad range of diameters to be held simply and securely.

12 Claims, 2 Drawing Sheets

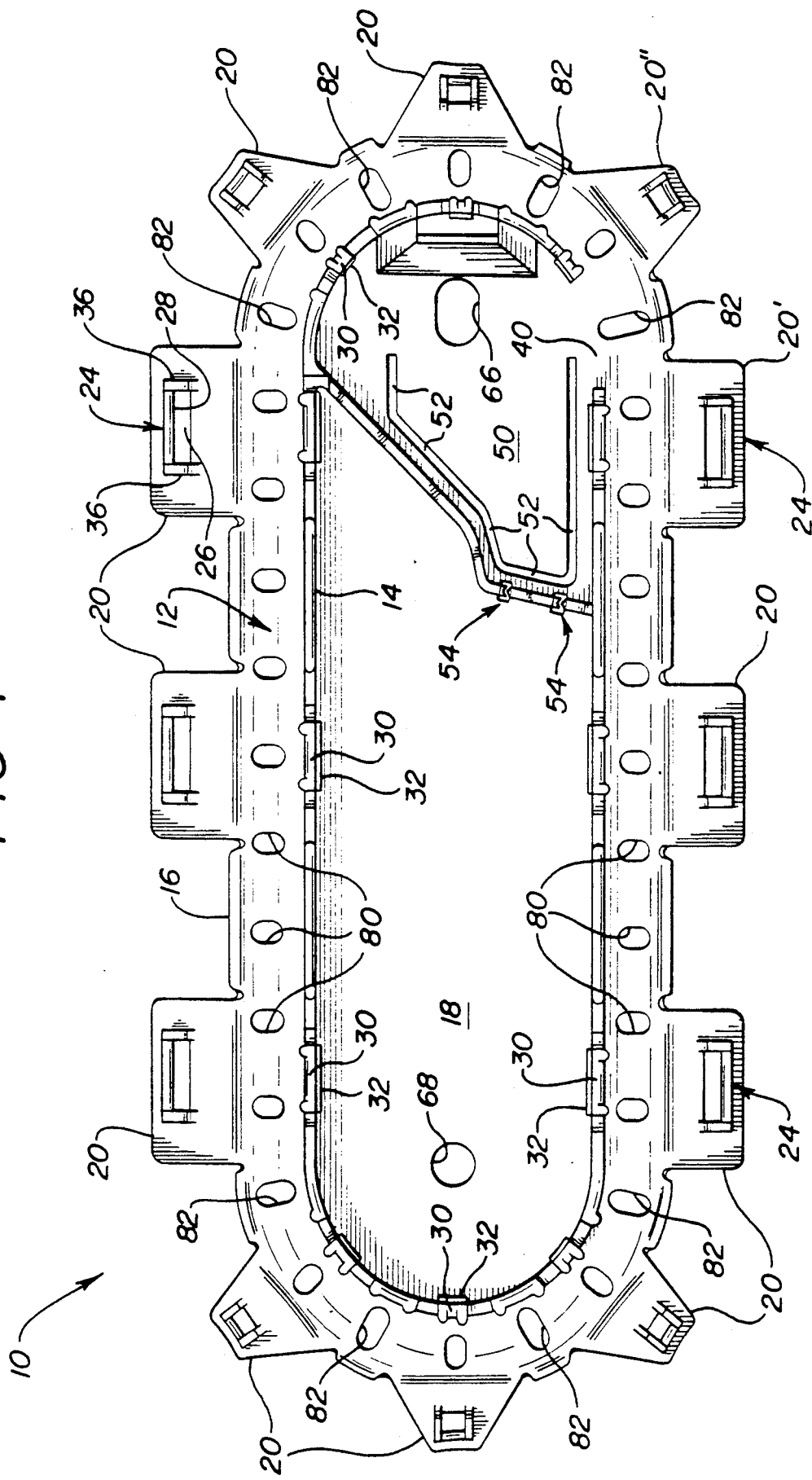

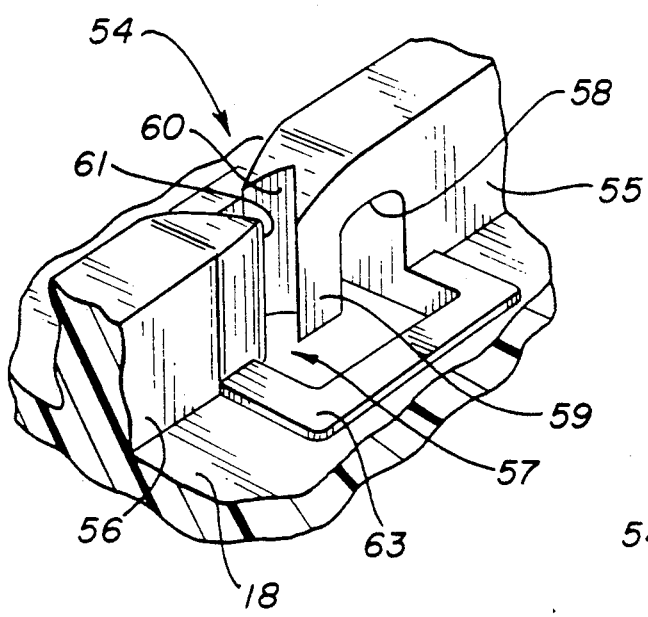
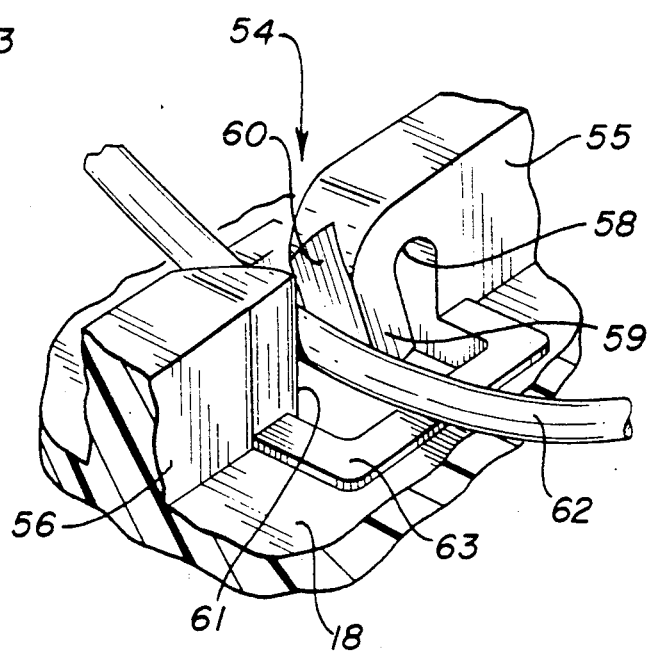
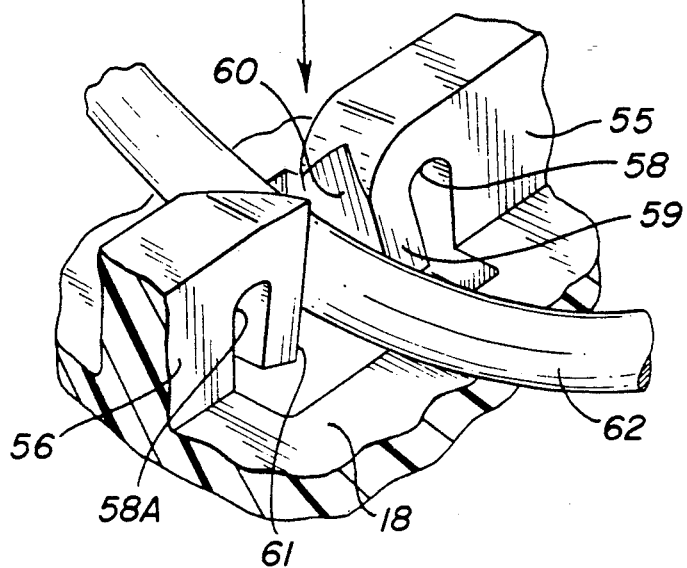

NEEDLE PARK

BACKGROUND OF THE INVENTION

1. Field of the Invention

This invention relates to a needle park for securing needles, and, more particularly, to a needle park for a package that holds one or more surgical needles and sutures.

2. Description of the Related Act

Packages for surgical needles and sutures must, among other things, securely anchor the needles, yet permit them to be easily removed when they are to be used. A simple holder device (i.e., needle park) for accomplishing that consists of a foam strip adhered to the base of the package. The needle either pierces the foam or is inserted into a slit cut into the foam. A disadvantage of the foam strip is that it is a separate element from the rest of the package and must be adhered to the base of the package, requiring an additional operation during package manufacture.

U.S. Pat. No. 4,961,498, issued Oct. 9, 1990, to Kalinski et al. discloses an alternate needle park comprising a molded post and adjacent molded rail, which may both be formed on the floor of a suture package. The post and rail are separated by a distance that is slightly smaller than the diameter of a needle to be held. When the needle is placed between the post and rail, the rail flexes slightly, and the needle is held in place by contact on either side of the needle with the post and the rail. This design is limited to holding needles of a single diameter. A somewhat similar needle park, which can hold a narrow range of needle diameters, is disclosed in U.S. Pat. No. 4,424,898.

A needle park adapted to hold needles having a broad range of diameters consists of a raised platform that has two string-like lengths arrayed parallel to each other, with their ends affixed to the platform. The strings have notched undersides and the platform is open below the strings. Needles are parked by insertion on top of the platform and under the strings. The notches on the strings prevent the needles from sliding along the length of the strings. This type of park can retain needles having a range of diameters; however, it depends on the flexibility of the strings and is not as simple or inexpensive to manufacture as are other needle parks.

U.S. Pat. No. 4,967,902, issued Nov. 6, 1990 to Sobel et al. discloses another type of needle park, comprising a wall that extends upward from the base of a needle package and that is interrupted by a gap into which the needle may be inserted. That type of park can only hold a needle whose diameter is substantially the same as the width of the gap between the wall ends. To increase the range of needle diameters that can be held, the wall ends can be undercut near the base and the base beneath the gap can be removed, which permits the wall ends to flex and bend, thereby accommodating a somewhat wider range of needle diameters. The range of needle diameters that can be held securely is limited, however.

SUMMARY OF THE INVENTION

In accordance with the present invention, a needle park for securing a needle comprises a generally planar base, on which is a first wall, generally perpendicular to the base and having near one end a cutout that separates an end section of the wall from the base and separates all but a top segment of the end section from the rest of the wall; and a second wall, generally perpendicular to the base, generally collinear with the first wall, and having a first end adjacent to the end section of the first wall, whereby the needle may be secured between the end section of the first wall and the first end of the second wall.

In another embodiment, a needle park for securing a needle comprises a generally planar base on which are two generally collinear walls, generally perpendicular to the base and separated by a gap, each wall having, near that end of the wall which adjoins the gap, a cutout that separates an end section of the wall from the base and separates all but a top segment of the end section from the rest of the wall, whereby the needle may be secured in the gap between the end sections.

The needle park of the present invention is adapted for being molded as part of a needle and suture package, which permits the packages to be made simply and inexpensively. At the same time, a single park can hold securely a needle whose diameter may vary over a broad range.

BRIEF DESCRIPTION OF THE DRAWINGS

FIG. 1 depicts a surgical needle and suture package of the present invention.

FIG. 2 is an isometric view of a needle park of the present invention.

FIG. 3 shows a needle secured in the needle park of FIG. 2.

FIG. 4 shows a needle secured in a needle park of another embodiment of this invention.

DETAILED DESCRIPTION OF THE INVENTION

The needle park of the present invention is adapted to securely anchor a surgical needle whose diameter is anywhere within a broad range of diameters. The needle park is typically part of a needle and suture package, and it does not unduly interfere with removal of the needle from the package. At the same time, the needle park is economical to manufacture. Thus, a suture package using this needle park can be manufactured by molding, stamping, or thermoforming of thermoplastic materials.

FIG. 1 is a plan view of a one-piece needle and suture package of the present invention. The package 10 includes a central floor area 18 which is surrounded by an outer oval channel 12 having two opposing straight sections connected by two semicircular end sections. The channel is defined by an inner wall 14 which extends upwardly from the floor area. The bottom and outer periphery of the channel 12 is defined by a curved section 16 of the package, which extends outwardly from the inner wall 14 at the level of the floor 18 and curves upwardly to approximately the elevation of the inner wall 14. Attached at the outer periphery of the curved section 16 are a plurality of hinged doors 20. The doors are hinged at an elevation which is slightly below the uppermost elevation of the outer periphery of the curved section and the inner wall so that, when the doors are folded over the channel and latched in place, the upper surfaces of the doors will align with the upper elevation of the outer periphery and inner wall. Formed in each door is a portion of the door locking means 24, including a latch opening 26 bounded by a door latch projection 28 and two fins 36. When the door is closed over channel 12, the top of the latch post 30 engages the door latch opening 26 and the door latch projection 28 hooks around the latch post projection 32 to lock the door in the closed position.

Located inside the oval channel is a needle park, an enlarged view of which appears in FIG. 2 and is described below. Adjacent the needle park is a relief flap 50 defined by a cutout 52. A portion of the inner wall 14 is eliminated in the vicinity of the needle park to form a vent 40 in the channel wall through which the suture of the needle accesses the channel between doors 20' and 20".

The bottom of the channel 12 formed by the curved section 16 is periodically perforated by holes 80 and 82 around the circumference of the channel. These holes are used for assembling the package with a suture and, optionally, a needle, as follows: Package 10 is placed on an assembly platform that has a number of upwardly extending pins. Two of the pins are aligned to extend upward through holes 66 and 68 in the center of the package to retain the package in its assembly position on the platform. Eight other pins extend upward and are aligned to pass through the holes 82 of the channel. The platform is open beneath the remaining channel holes 80 and a vacuum source below the platform draws air through the holes 80. With the package so emplaced, the needle is located in the needle holder, and the suture is looped above the pin extending through hole 66 then downward through the vent 40 and into the channel. The suture is then wound in a clockwise direction around the pins which extend through the channel holes 82.

Additional details regarding the construction of the suture package of FIG. 1 appear in U.S. Pat. No. 4,967,902, incorporated herein by reference.

FIG. 2 shows an enlarged isometric view of needle park 54. The needle park includes a first wall 55 and a second wall 56, both generally perpendicular to the floor 18 and separated by a gap 57. Cutout 58 separates end section 59 from base 18 and separates all but a top segment of end section 59 from the rest of wall 55. Preferably the upper surface of the top segment and the top of wall 56, on the opposite side of gap 57, are tapered to guide a needle.

In the embodiment shown, the separation of end section 59 from base 18 is a result of extending cutout 58 downward to include the region of base 18 that lies between walls 55 and 56. In an alternative embodiment, base 18 remains intact, but the bottom of end section 59 is cut off. The embodiment shown, with the cutout including a portion of the base, is preferred, because it is easier to form by molding, a preferred method of fabricating package 10.

The facing surfaces of walls 55 and 56 preferably have complementary shapes that maintain substantially constant separation over their surfaces. In the embodiment of FIG. 2, the facing surface of wall 55 has a "V"-shaped groove 60 that runs vertically from the top to the bottom of the wall, and the facing surface of wall 56 has a complementary top-to-bottom extension 61. An advantage of providing non-planar complementary faces on the adjoining surfaces of the walls is that a very small effective separation (essentially zero) can be achieved, which, in turn, permits very thin needles to be held. Furthermore, the "3-point contact" (to the needle) that is provided by the facing surfaces of FIG. 2 helps to prevent a needle from sliding in the needle park. Needle sliding can be a particular problem when there are closely adjoining needle parks—as shown in FIG. 1. In that case, sliding can cause the needles in adjoining parks to come into contact with each other, which is undesirable.

FIG. 3 shows part of a needle 62 being held in a needle park of the type shown in FIG. 2. The top segment of end section 59 has become a pivot point and the bottom of end section 59 has been bent into cutout 58 to accommodate needle 62. The substantially fixed top segment and flexible bottom of end section 59 combine to provide an "undercut" that minimizes the risk of the needle inadvertently backing out of the needle park. For holding very-small-diameter needles, the floor area 63 that supports the needle on opposite sides of gap 57 may be slightly raised, as shown in FIGS. 2 and 3, to prevent the needle from sliding between floor 18 and the bottom of end section 59.

FIG. 4 shows another embodiment of a needle park of this invention, particularly adapted for holding large-diameter needles. In this embodiment, the second wall 56 also has a cutout 58A. As a result, both walls have end sections with a top segment that provides a pivot point and a bottom that bends into a cutout. Compared to the embodiment shown in FIG. 3, the two-cutout structure is more symmetrical, and thus permits the hinge formed by the top of the end section to be stiffer.

The material of package 10 and of needle park 54 is preferably a moldable thermoplastic. Polypropylene is preferred, because of its flexibility, moldability, and ability to form a "living hinge" at end section 59. The dimensions of the elements of the needle park—e.g., gap width, size of cutout, dimensions of the groove and extension on the adjoining surfaces of the walls, etc.—are determined by the range of dimensions of the needles to be held and the mechanical characteristics of the needle park material—e.g., strength, flex modulus, memory, etc.

The invention having been described in specific detail and the manner in which it may be carried out having been exemplified, it will be readily apparent to those skilled in the art that innumerable variations, applications, modifications, and extensions of the basic principles involved may be made without departing from the spirit or scope of the invention.

I claim:

1. A needle park for securing a needle, comprising a generally planar base, on which is
   a first wall, generally perpendicular to the base and having near one end a cutout that separates an end section of the wall from the base and separates all but a top segment of the end section from the rest of the wall; and
   a second wall, generally perpendicular to the base, generally collinear with the first wall, and having a first end adjacent to the end section of the first wall, whereby the needle may be secured between the end section of the first wall and the first end of the second wall.

2. The needle park of claim 1 in which the end section of the first wall and the first end of the second wall have adjoining facing surfaces that have complementary shapes, with substantially constant separation over the surfaces.

3. The needle park of claim 2 in which the facing surface of the end section of the first wall has a generally vertical groove that generally extends from the top of the surface to the bottom and that adjoins a generally top-to-bottom extending projection on the facing surface of the first end of the second wall.

4. The needle park of claim 1 in which the base is cut away in the region below and between the first and second walls.

5. The needle park of claim 1 in which the material of the park comprises a thermoplastic.

6. The needle park of claim 5 in which the material of the park is polypropylene.

7. A package for a surgical needle and suture, comprising the needle park of claim 1.

8. A needle park for securing a needle, comprising a generally planar base on which are two generally collinear walls, generally perpendicular to the base and separated by a gap, each wall having, near that end of the wall which adjoins the gap, a cutout that separates an end section of the wall from the base and separates all but a top segment of the end section from the rest of the wall, whereby the needle may be secured in the gap between the end sections.

9. The needle park of claim 8 in which the end sections of the walls have facing surfaces that have complementary shapes, with substantially constant separation over the surfaces.

10. The needle park of claim 8 in which the base is cut away in the gap between the walls.

11. The needle park of claim 8 in which the material of the park comprises a moldable thermoplastic.

12. A package for a needle and suture comprising the needle park of claim 8.

* * * * *